US00PP12462P2

(12) United States Plant Patent
Noodelijk

(10) Patent No.: US PP12,462 P2
(45) Date of Patent: Mar. 12, 2002

(54) CHRYSANTHEMUM PLANT NAMED 'HALIFAX'

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 09/561,925

(22) Filed: May 1, 2000

(51) Int. Cl.[7] ..... A01H 5/00
(52) U.S. Cl. ..... Plt./294
(58) Field of Search ..... Plt./294

*Primary Examiner*—Bruce R. Campell
*Assistant Examiner*—Annette H. Para
(74) *Attorney, Agent, or Firm*—Parkhurst & Wendel, L.L.P.

(57) ABSTRACT

A Chrysanthemum plant named 'HALIFAX' characterized by its large sized blooms with white ray-florets and a green-white cushion center disc florets.

2 Drawing Sheets

RELATED CULTIVARS

'HALIFAX' is related to 'HALIFAX' YELLOW (U.S. plant application Ser. No. 09/561,936). 'HALIFAX' YELLOW is a mutant from 'HALIFAX'.

BACKGROUND OF THE INVENTION

'HALIFAX' is a product of a breeding-program which had the objective of creating new chrysanthemum cultivars with a anemone type flower, a 7 week response and a medium plant height. The new plant of the present invention comprises a new and distinct cultivar of Chrysanthemum plant. 'HALIFAX' is a seedling from a cross in a breeding program maintained under the control of inventor. The female parent is #94.0898—unpatented—, the male parent is #93.0607 —unpatented—, both unamed seedlings not available to inventor for description. The new and distinct cultivar was discovered and selected as a flowering plant within the progeny of the stated cross by Rob Noodelijk in a controlled environment (greenhouse) in Rijsenhout Holland in September 1997. The first act of asexual reproduction of 'HALIFAX' was accomplished when vegetative cuttings were taken from the initial selection in December 1997 in a controlled environment in Rijsenhout Holland.

SUMMARY OF THE INVENTION

The present invention is a new and distinct variety of chrysanthemum bearing large sized blooms with white ray-florets and a green-white disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
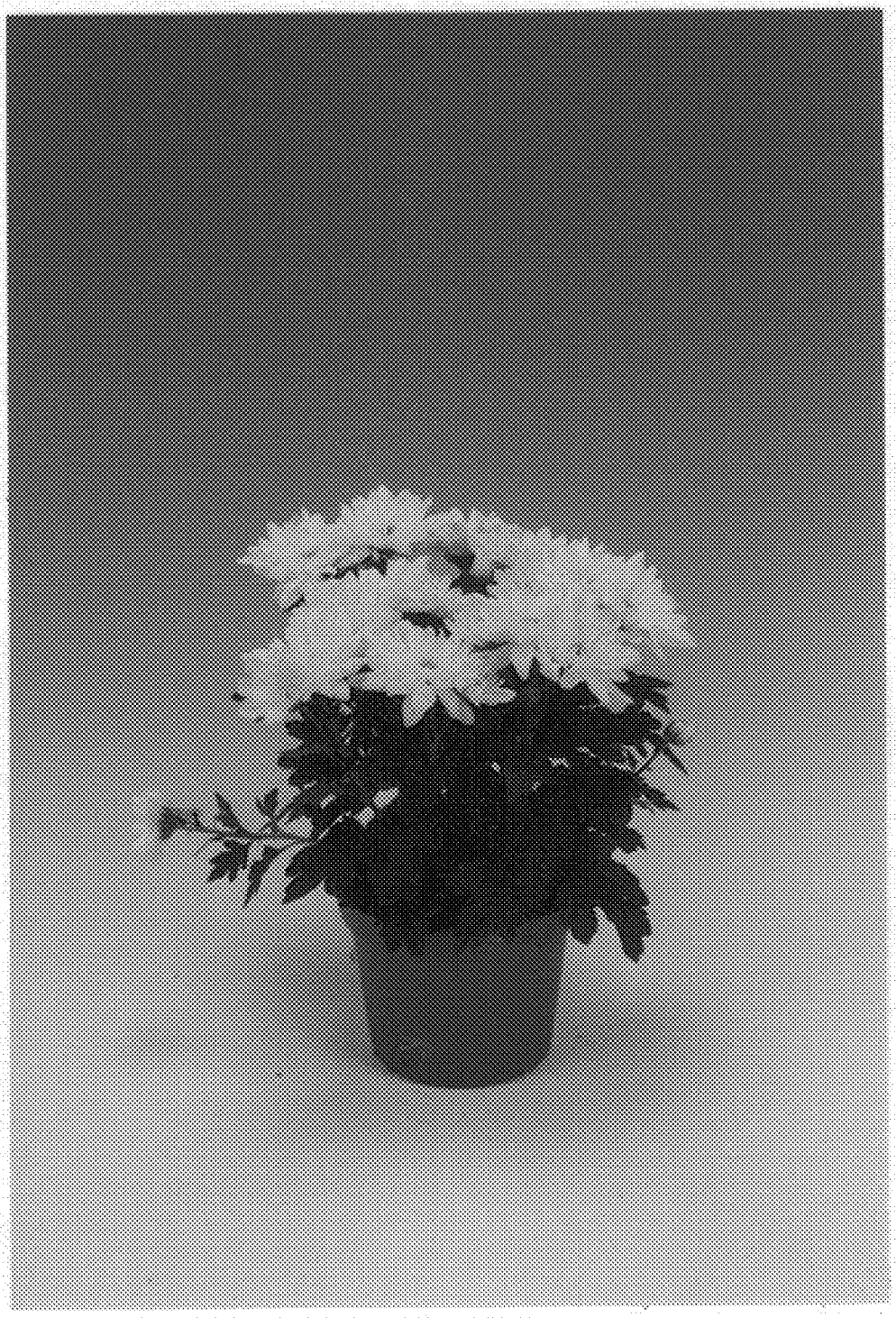
FIG. 1 shows a plant of the cultivar in full bloom.
Figure 2:
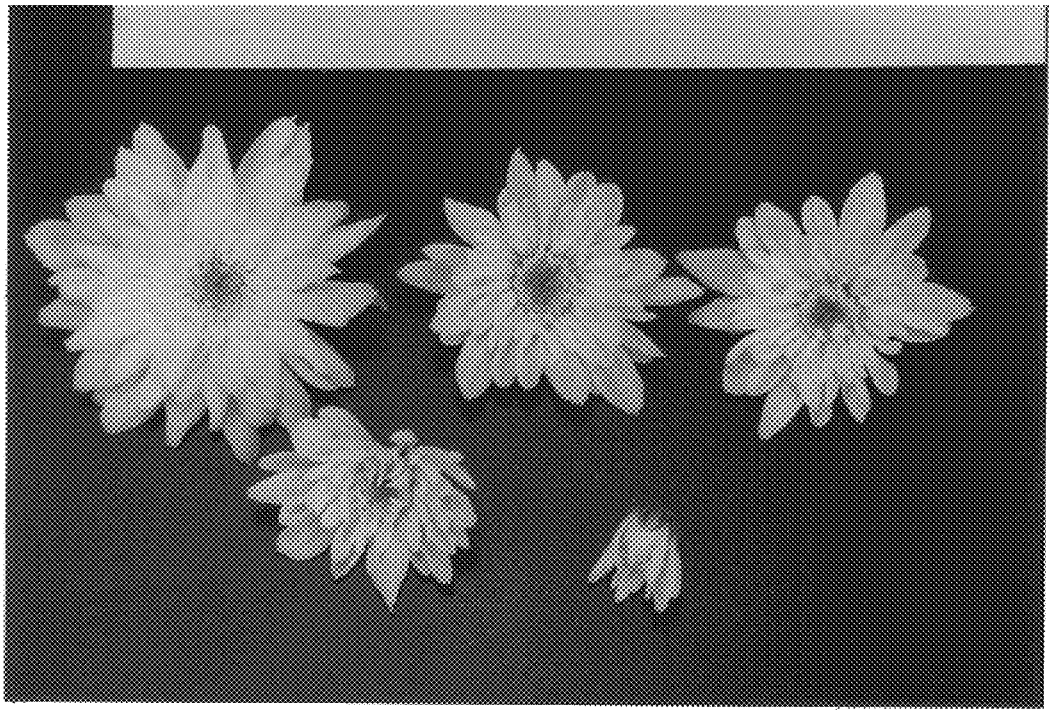
FIG. 2 shows the various stages of bloom of the new cultivar.
Figure 3:
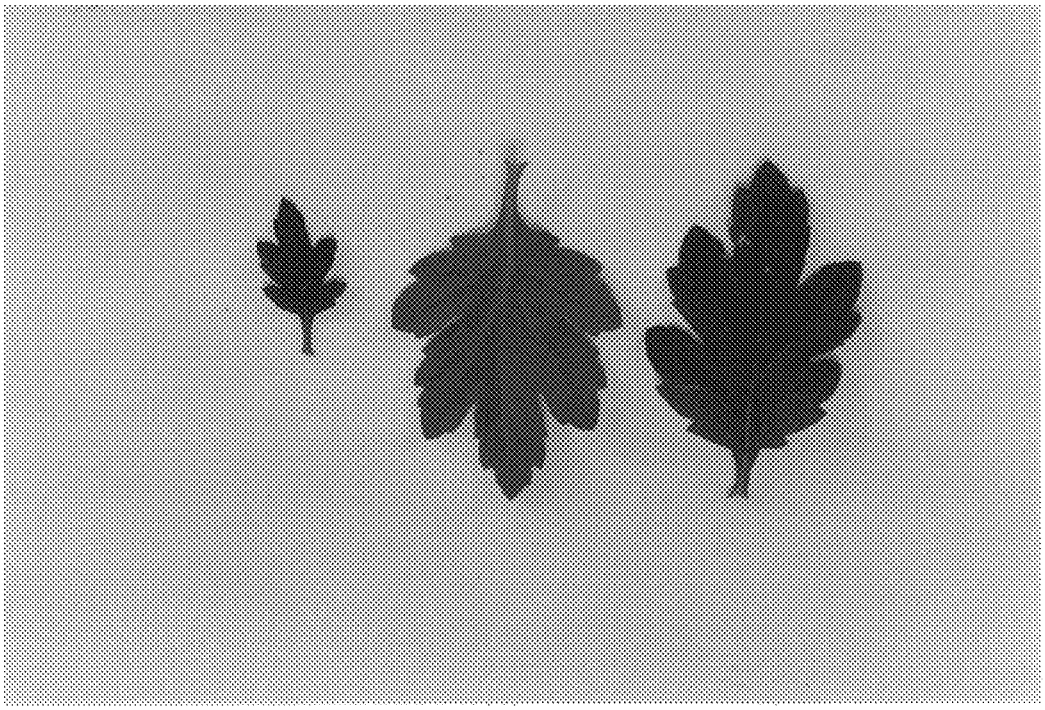
FIG. 3 shows the foliage of the new cultivar.

This new variety of chrysanthemum is of the botanical classification *dendranthema grandiflora*. The observations and measurements were gathered from 54 days plants grown in a greenhouse in Rijsenhout Holland in a photo-periodic controlled crop under conditions generally used in commercial practice. The greenhouse temperatures during this crop were at day-time between 18° C. and 25° C. and at night 20° C. The photo-periodic response time in this crop was 55 days after an average of eight long days. After this long day period to flowering growth retardants were applied 6 times in an average dose of 1.5 gram/liter water. No tests were done on disease or insect resistance or susceptibility. This new variety produces large sized blooms with white ray-florets and a green-white cushion center disc-florets blooming on the plant for 5 weeks. This new variety of chrysanthemum has been found to retain its distinctive characteristics throughout successive propagations however the phenotype may vary significantly with variations in environment such as light intensity and temperature. To show the phenotype as described 'HALIFAX' can be planted without assimilation lightning (high pressure sodium lamps) between week 50 and week 40 of the next year under greenhouse conditions in Holland. With assimilation lightning (minimum level 2500 lux) it can be planted year round under greenhouse conditions in Holland.

From the cultivars known to inventor the most similar existing cultivar in comparison to 'HALIFAX' is 'HALIFAX' YELLOW. When 'HALIFAX' YELLOW and 'HALIFAX' are being compared the following difference is noticed: The difference of 'HALIFAX' YELLOW and 'HALIFAX' is the ray-floret color. 'HALIFAX' is white 155 D, 'HALIFAX' YELLOW is yellow 7 A. Inventor does not known any other commercial available variety that is comparable with 'HALIFAX'.

The following is a description of the plant and characteristics that distinguish 'HALIFAX' as a new and distinct variety.

The color designations are taken from the plant itself. Accordingly, any discrepancies between the color designations and the colors depicted in the photographs are due to photographic tolerances. The color chart used in this description is: The Royal Horticultural Society color chart, edition 1995.

Botanical Description of CULTIVAR 'HALIFAX'

Bud:

*Size.*—Large ;cross-section 1.5 cm, height 1.5 cm.

*Outside color.*—White 155 D.
*Involucral bracts.*—2 rows, length 7 mm, width 3 mm.
*Involucral bracts among disc-florets.*—Not present.
*Involucral bracts color.*—Yellow-green 147 B.

Bloom:
*Type.*—Anemone.
*Height.*—Medium high.
*Size.*—Large.
*Fully expanded.*—7.0 cm.
*Number of blooms per branch.*—Approx. 4–5 blooms per branch.
*Performance on the plant.*—5 weeks.
*Seeds.*—Not produced.
*Fragrance.*—Typical chrysanthemum.

Color:
*Center of the flower* (*disc-florets*).—Immature yellow-green 144 A. Mature white 155 D and yellow-green 146 D in the center.
*Color of upper surface of the ray-florets.*—White 155 D.
*Color of the lower surface of the ray-florets.*—White 155 D.
*Tonality from distance.*—A pot mum with large semi-double pure white flowers and a green disc.
*Discoloration to color.*—The green part of the center to yellow-green 146 D.

Ray florets:
*Texture.*—Upper and under side smooth.
*Number.*—42–45 (3 rows).
*Cross-section.*—Flat.
*Longitudinal axis of majority.*—Straight.
*Length of corolla tube.*—Short.
*Ray-floret margin.*—Entire.
*Ray-floret length.*—3.3–3.6 cm.
*Ray-floret width.*—0.9–1.1 cm.
*Ratio length / width.*—Medium.
*Shape of tip.*—Dentate.

Disc florets:
*Disc diameter.*—2.5 cm.
*Distribution of disc florets.*—Numerous clearly visible at all stages of flowering.
*Shape.*—Petaloid.
*Color.*—White 155 D, yellow-green 146 D at the tip.
*Receptacle shape.*—Domed raised.

Reproductive organs:
*Stamen* (*present in disc florets only*).—Green, thin, 4 mm. In length.
*Number of stamen.*—Grown together as one.
*Stamen color.*—Yellow-green 144 B.
*Pollen.*—None.
*Pollen color.*—Not applicable.
*Styles* (*present in both ray and disc florets*).—Green, thin.
*Style color.*—Yellow-green 144 B.
*Style length.*—5 mm.
*Stigmas.*—Green-yellow.
*Stigma width.*—2 mm.
*Ovaries.*—Enclosed in calyx.

Plant:
*Form.*—A pot mum meant for indoor use.
*Growth habit.*—Spreading.
*Growth rate.*—Moderate.
*Height.*—23–25 cm.
*Width.*—25–27 cm.
*Stem color.*—Yellow-green 147 B.
*Stem strength.*—Strong.
*Stem brittleness.*—Absent.
*Stem anthocyanin coloration.*—Absent.
*Length of lateral branch.*—From top to bottom 12–13 cm.
*Lateral branch color.*—Yellow-green 147 B.
*Lateral branch, attachment.*—Strong.
*Branching* (*average number of lateral branches*).—Normal with 3–4 breaks after pinching.
*Penduncle length.*—2.5–3.0 cm.
*Peduncle color.*—Yellow-green 147 B.
*Flowering response* (*photo-periodic controlled crop, not natural season.*—55 Days.

Foliage:
*Color.*—Upper side green 139 A. Under side yellow-green 146 A.
*Size.*—Large; length 7.0 cm, width 5.0 cm.
*Quantity* (*number per lateral branch*).—7–9.
*Shape.*—Oval.
*Texture upper side.*—Glabrous.
*Texture under side.*—Pubescent.
*Venation arrangement.*—Palmate.
*Shape of the margin.*—Serrated.
*Shape of base of sinus between lateral lobes.*—Acute.
*Margin of sinus between lateral lobes.*—Diverging.
*Shape of base.*—Rounded.
*Apex.*—Mucronate.

Differences with the comparison varieties

| | 'HALIFAX' | 'HALIFAX YELLOW' |
|---|---|---|
| Ray-floret color | White 155 D | Yellow 7A |

I claim:

1. A new and distinct variety of chrysanthemum plant as described and illustrated.

* * * * *